United States Patent [19]

Spraggins

[11] 4,045,577

[45] Aug. 30, 1977

[54] VALUABLE MEDICINIAL PROSTAGLANDIN COMPOUNDS PREPARED FROM MATERIAL ISOLATED FROM THE SEA

[75] Inventor: Robert L. Spraggins, 1105 Mary Oaks, College Station, Tex. 77840

[73] Assignee: Alza Corporation, Palo Alto, Calif.

[21] Appl. No.: 597,212

[22] Filed: July 18, 1975

Related U.S. Application Data

[63] Continuation of Ser. No. 154,193, June 17, 1971, abandoned.

[51] Int. Cl.$^2$ ............... A61K 31/215; A61K 31/19; C07C 177/00
[52] U.S. Cl. .................. 424/311; 260/410.9 R; 260/468 D; 260/465 L; 260/488 R; 260/514 D; 424/305; 424/317
[58] Field of Search .......... 260/468 D, 514 D, 488 R; 424/311

[56] References Cited

U.S. PATENT DOCUMENTS

| | | | |
|---|---|---|---|
| 3,558,682 | 1/1971 | Pappo et al. | 260/468 |
| 3,736,319 | 5/1973 | Marte et al. | 260/240 |
| 3,755,565 | 8/1973 | Spraggins | 424/101 |
| 3,849,474 | 11/1974 | Abraham et al. | 260/468 |

FOREIGN PATENT DOCUMENTS

| | | | |
|---|---|---|---|
| 7,309,856 | 1/1974 | Netherlands | 260/468 |

OTHER PUBLICATIONS

Advances in Organic Chemistry 3, pp. 218-221 (1963).
Remington's Pharmaceutical Sciences p. 1599 (1970).

*Primary Examiner*—Robert Gerstl
*Attorney, Agent, or Firm*—Paul L. Sabatine; Steven D. Goldby

[57] ABSTRACT

Novel compounds of the formula

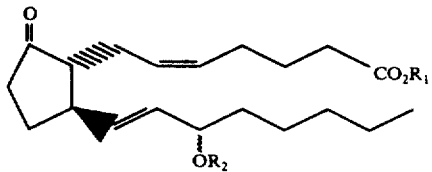

wherein $R_1$ is hydrogen or alkyl, $R_2$ is hydrogen or acyl, the diastereomers and the pharmaceutically acceptable salts. The compounds are prepared by the hydrogenation and epimerization of naturally occurring inactive prostaglandins and they are useful as antihypertensive agents and as intermediates for preparing other prostaglandins possessing therapeutic properties.

1 Claim, No Drawings

VALUABLE MEDICINIAL PROSTAGLANDIN COMPOUNDS PREPARED FROM MATERIAL ISOLATED FROM THE SEA

This is a continuation, of application Ser. No. 154,193, filed June 17, 1971, now abandoned.

BACKGROUND OF THE INVENTION

The present invention relates to novel and useful prostaglandins and to a chemical process for preparing same. More particularly, the invention pertains to new prostaglandin compounds represented by Formula 1 of the following general formula:

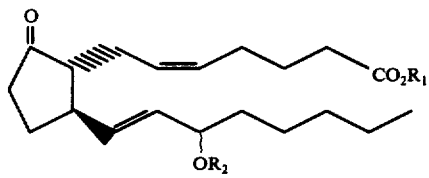

wherein $R_1$ is a member selected from the group consisting of hydrogen and lower alkyl, $R_2$ is a member selected from the group consisting of hydrogen and acyl of 1 to 18 carbon atoms inclusive, the diastereomers and the non-toxic, pharmaceutically acceptable salts. The compounds are prepared from naturally occurring prostaglandins by the selective hydrogenation of carbon to carbon double bonds followed by epimerization of biologically inactive groups to biologically active groups and by the reaction of carboxyl groups and hydroxyl groups with saltifying and esterifying agents to produce the novel compounds of Formula 1. The compounds of Formula 1 are useful as antihypertensive agents and also as intermediates for preparing other prostaglandins possessing therapeutic properties.

In the present disclosure and the accompanying claims the definitions of symbols and terms in the foregoing formula and where they appear elsewhere throughout this specification and the accompanying claims, their usage thereof has the following significance:

By "lower alkyl" is meant straight or branched chain alkyl radicals of 1 to 8 carbon atoms inclusive, such as, methyl, ethyl, n-propyl, iso-propyl, n-butyl, sec-butyl, pentyl, neo-pentyl, n-hexyl, iso-hexyl, heptyl, n-octyl, 4,4-dimethyl pentyl, 2-ethyl hexyl, 2,2,4-trimethylpentyl, and the like.

Exemplary of "acyl" groups are the acyl groups having from 1 to 18 carbon atoms inclusive such as alkanoyl, alkenoyl, aroyl, substituted derivatives thereof, and the like. Typical alkanoyl groups include formyl, valeryl, acetyl, propionyl, heptanoyl, actanoyl, undecanoyl, lauroyl, palmitoyl, stearoyl, oleoyl, isomeric forms thereof, and the like; typical alkenoyl groups include acryloyl, methacryloyl, crotonyl, 3-butenoyl, β-methyl-α-butenoyl, and the like; typical aroyl groups such as benzoyl, phenylacetyl, cinnamoyl, naphthoyl, p-ethoxybenzyl, allyloxyphenylacetyl, and the like. Examples of other acyl moieties within the scope of the invention are carboxacyl moieties such as cyclohexanecarbonyl, 3-cyclohexanecarbonyl, p-chlorophenoxyacetyl, succinyl, p-nitrobenzoyl, furoyl, 3-pyridinecarbonyl, and the like.

The phase "pharmaceutically acceptable" or "non-toxic salts" as used herein generally includes the non-toxic alkali metal and the non-toxic alkaline earth bases such as sodium, potassium, calcium, lithium, copper and magnesium, the hydroxides and the carbonates thereof, the ammonium salts and the substituted ammonium salts, for example, the non-toxic salts of trialkylamines such as triethylamine, trimethylamine, tri-isopropylamine, tri-n-propylamine, tri-n-butylamine, and other amines such as morpholine, diethylamine, dimethylamine, methyl-cyclohexylamine, ethylcyclohexylamine, glucosamine, procaine, dibenzylamine, triethanolamine, N-benzyl-β-phenylethylamine, ethyldimethylamine, tripropanolamine, N-benzyl-β-phenylmethylamine, ethyldipropylamine, ethyldiisopropylamine, benzylamine, p-ethoxybenzylamine, N-(lower)alkyl piperidines, such as N-ethylpiperidine, N-isopropylpiperidine, N-methylpiperidine and other pharmaceutically acceptable amines. Also, the non-toxic salts of Formula 1 with monoalkyl and dialkylamines, and tetra-alkylammonium hydroxides. The latter are art called therapeutically acceptable quaternary ammonium salts.

The numbering system and the stereochemistry nomenclature used for the prostaglandin compounds of this invention is the art accepted numbering and nomenclature. That is, the cyclopentane ring of the prostenoic acid is numbered 8 through 12 inclusive for a 20 carbon naturally occurring or synthetic prostaglandin. The carboxyl side chain or its derivatives ($R_1$=H or alkyl) is bonded to the cyclopentane ring at the ring's 8 position, and the alkyl side chain is bonded to the cyclopentane ring at the ring's 12 position. The stereochemistry of the substituents on the cyclopentane ring, when shown, may be α-oriented or β-oriented, that is, α-substituents are oriented on the same side of the cyclopentane ring as the carboxyl side chain, and β-substituents are oriented in the opposite sense or on the same side as the alkyl side chain. The substituents bonded to the alkyl side chain may have a sinister (S) or rectus (R) configuration which is equivalent to α and β respectively, in the projection formula used here. In the formulae used herein, a broken line indicates an α-configuration, a solid wedge indicates a β-configuration and a wavy line indicates that these substituents are in the α-configuration or the β-configuration. The numbering system and stereochemistry is reported in *Progess in the Chemistry of Fats and Other Lipids*, Vol IX, pages 233 to 236, Pergamon Press, New York; and, *J. Lipids Research*, Vol. 10, pages 316 to 319, 1969.

DESCRIPTION OF THE INVENTION

The novel compounds of Formula 1

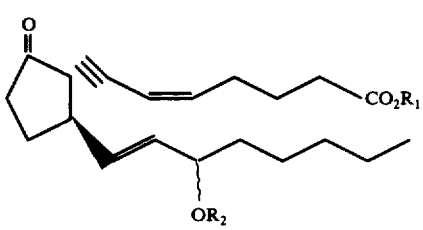

Formula 1 wherein $R_1$ and $R_2$ are as previously defined, its carboxylate esters, alcoholic esters, salts, diastereomers, enantiometers are prepared from 15(R)-hydroxy-9oxo-5-cis,10,13-trans-prostatrienoic acid, its mono and diesters, and salts thereof embraced by Formula 2:

Formula 2

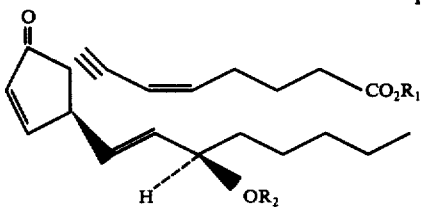

wherein $R_1$ and $R_2$ are as defined above.

The starting compounds used for the purpose of this invention, as illustrated by generic Formula 2, for example, lower alkyl 15(R)-acyloxy-9-oxo-5-cis,10,13-trans-prostatrienoate and its alcohol and acid derivatives, specifically, methyl 15(R)-acetoxy-9-oxo-5-cis,10,13-trans-prostatrienoate, that is isolated from the gorgonian, *Plexaura homomalla* (Esper). The *Plexaura homomalla* consists of two parts, an outer cortex and an inner skeleton. The compounds of the Formula 2 can be isolated from the intact gorgonian or from its outer cortex. The cortex can be easily separated from the skeleton in either a wet or dry form. When the dry form is employed, the gorgonian is air dried for several days at room temperature and the cortex stripped from the skeleton. Next, the cortex is ground to a fine mesh size in a conventional laboratory grinder. The resulting ground material is then extracted with an organic solvent, such as hexane, petroleum ether and the like, or with an aqueous media that forms an aqueous emulsion that itself can be extracted with an organic solvent to produce an crude extract of the gorgonian, *Plexaura homomalla*. The crude extract is next separated by chromatographic procedures, for example, column chromatography, thin layer chromatography, paper chromatography or the like to obtain the starting compounds. The isolation of prostaglandin derivatives from *Pexaura homomalla* is reported in *Tetrahedron Letters*, No 59, pages 5185 to 5188, 1969.

The next step in the preparation of the novel compounds of Formula 1 consists in chemically contacting and selectively hydrogenating the ethenoid double bond or bonds present in the compounds of Formula 2, for example, the carbon to carbon double bond in the cyclopentane ring, or the carbon carbon double bond in the carboxylic acid side chain, or both, to produce saturated carbon to carbon bonds. Hydrogenation of the ethylenic double bond or bonds is achieved without adversely effecting the total compound by using hydrogenation catalysts in the presence of a non-hydroxylic organic solvent, and exposing the reaction mixture to hydrogen. The hydrogenation is carried out at temperatures from −70° C to 100° C, or higher, usually from 0° to 25° C, and at atmospheric pressure or higher atmospheric pressures up to 15 atmospheres. The hydrogenation is allowed to continue until one mole of hydrogen is consumed for the saturation of one carbon to carbon double bond, or two moles or more of hydrogen for the saturation of two or more ethylenic double bonds. Generally, about 5 to 30% by weight of catalysts is employed, although good results are obtained with smaller or larger quantities. Examples of catalysts suitable for the hydrogenation process include noble metal catalysts, for example, palladium or rhodium, usually rhodium on alumina, rhodium on carbon, palladium on charcoal, palladium on carbon, chlorotris (triphenylphosphine)rhodium, and the like. Examples of non-hydroxylic organic solvents suitable for the reaction medium include inert organic solvents such as ethyl acetate, ethylene glycol, dimethyl ether, tetrahydrofuran, dioxane, benzene, toluene, methanol and the like. When the hydrogenation is completed, the hydrogenated product is recovered by eliminating the catalyst by filtration and the solvent evaporated to dryness, or the desired product can be conveniently recovered by first neutralizing the catalyst by diluting the reaction medium with water and extracting with a water immiscible solvent such as methylene chloride, cyclohexane, benzene and the like; then, washing with alkali and employing chromatography on synthetic magnesium silicate, silica gel or the like, or by distillation or other conventional recovery processes to yield the hydrogenated product.

Next, the substituents at the C-15(R) of the hydrogenated prostatrienoic acid or its derivatives are converted to the corresponding diastereoisomeric C-15 esters by epimerization comprising chemically contacting and reacting the hydrogenated compound with at least stoichiometrically equivalent amounts or with an excess of from 1 to about 10 or more molecular equivalents of an aliphatic acid of the formula $C_nH_{2n+1}COOH$ wherein $n$ is 0 to 5 inclusive, and in the presence of trace to equal molar quantities or an excess thereof of the acid's corresponding alkali metal or alkaline earth metal salt of the general formula $(C_nH_{2n+1}CO_2)_xM$ wherein M is an alkali metal or an alkaline earth metal and $x$ is 1 or 2, to produce from the selectively hydrogenated derivatives of Formula 2, the corresponding diastereoisomeric C-15 esters. The alkali metal salt or the alkaline earth metal salt can be added directly to the reaction comprising the hydrogenated form embraced by Formula 2 and the aliphatic acid or it can be formed in situ by the reaction of at least equal molar amounts of the aliphatic acid with equal molar amounts or an excess thereof of an alkali metal base or alkaline earth metal base of the formula $M(OH)_x$ where M and $x$ are as defined above. The C-15 esters are generally produced at a temperature of about 10° C to 40° C, at a pressure of 1 atmosphere to 10 atmosphere, with an accompanying reaction period of about 5 minutes to about 66 hours, and the like.

The diastereoisomeric C-15 esters can be next converted to the corresponding diastereoisomeric C-15 hydroxylates by hydrolyzing the respective ester with at least stoichiometric amounts or with an excess thereof of a lower alkanol and in the presence of a small amount of an acid catalyst to produce the diastereoisomeric C-15 hydroxylates. The hydrolyzing reaction can be carried out with or without stirring at temperatures from 0° C to 70° C for about ½ hour to 25 hours, at a pressure of 1 atmosphere to 5 atmosphere or higher, or until the formation of the diastereomeric C-15 hydroxylate is completed. The hydrolyzing reaction is usually carried out by gently stirring and warming the reaction mixture at about 5° C to 75° C to ensure a mixing of the reactants, and then allowing the reaction mixture to stand and the reactants to react at ambient temperature and pressure, usually 25° and 1 atmosphere for about 1 hour to 25 hours. The C-15 hydroxylates are recovered from the reaction medium by adding aqueous sodium chloride solution or saturated brine to the reaction mixture and then extracting the just formed aqueous reaction mixture with a water immiscible organic solvent. The separated organic solvent extract is evaporated to dryness to yield a mixture containing the diastereoisomeric C-15 hydroxylates.

The C-15 hydroxylates present in the mixture are separated from each other by first dissolving the mixture in an organic solvent, for example, benzene, and then washing the mixture onto a column comprising about 40 to 60 grams of column support, for example, silicic acid, silica gel and the like, for each gram of mixture containing the C-15 hydroxylates. The compounds are then chromatographically separated by eluting them from the column with an eluant, for example, 10% to 20% ethyl acetate in benzene fractions. Fractions of 75 to 125 mls are collected to obtain the purified C-15 hydroxyl compounds.

The diastereoisomeric hydroxylates can be separated using column chromatography on active column supports, such as acid washed silica gel, silicic acid, synthetic magnesium silicate, acidic alumina, neutral alumina, mixtures thereof, and the like, with elution of the diastereoisomers with lower alkanoates such as ethyl acetate, propyl acetate, methyl butyrate, mixtures thereof, mixtures of these with cyclohexane, benzene, ethanol, and the like, elutants consisting of ethyl acetate-hexane-water-methanol-acetic acid, ethyl acetate and more polar additives such as ethyl acetate-formic acid, ethyl acetate-acetone-acetic acid, cyclohexane-ethyl acetate-acetic acid and the like to yield the diastereoisomers; *J. Lipid Research,* Vol 10, pages 316 to 319, 1969.

Examples of aliphatic acid of the general formula $C_nH_{2n+1}COOH$ as defined above are acids such as formic, acetic, propionic, butyric, valeric, mixtures thereof, the isomeric forms thereof, and the like.

Examples of the alkali metal or alkaline earth metal salts of the general formula $(C_nH_{2n+1}CO_2)_xM$ are where M is a metal comprising Group IA of the periodic system comprising lithium, sodium, potassium, rubidium, and cesium; and also where M is a metal of Group IIA of the periodic system comprising calcium, strontium, barium and magnesium. Typical salts include sodium formate, sodium acetate, calcium propionate, barium valerate, lithium valerate, potassium butyrate, cesium lauroate, lithium acetate and the like.

Exemplary alkaline earth metal bases and alkali metal bases include lithium hydroxide, sodium hydroxide, potassium hydroxide, cesium hydroxide, calcium hydroxide, barium hydroxide, magnesium hydroxide, and the like.

Representative of lower alkanols of 1 to 8 carbons inclusive, of the straight or branched chain type, such as methanol, ethanol, iso-propanol, n-butanol, n-pentanol, hexanol, octanol, 1,1-dimethyl propanol, and the like.

Representative of acid catalysts suitable for performing the reactions are p-toluenesulfonic acid, hydrochloric acid, anhydrous hydrobromic acid, Lewis acids such as boron trifluoride, boron trifluoride etherate, boron trichloride etherate, stannic oxychloride, phosphorous oxychloride, phosphorous pentachloride, and the like. Representative of water-immiscible solvents generally include benzene, toluene, carbon tetrachloride, ether, cyclohexane, methylene chloride, and the like.

The carboxylate esters of the novel and useful prostaglandins of the invention are obtained by art known chemical procedures, for example, by reacting the prostaglandin (when $R_1,R_2=H$) with a solution containing a diazo(lower)alkane to produce the prostaglandin carboxylate ester. Esterification of the prostaglandin acid is performed by reacting the prostaglandin acid with the diazoalkane, for example, diazomethane, diazoethane, diazopropane, diazobutane, etc., in an inert organic solvent, for example, lower alkanols, symmetrical and unsymmetrical ethers, and halogenated solvents. Representative of suitable solvents are ethanol, methanol, propanol, diethyl ether, methylethyl ether, tetrahydrofuran, acetone, cyclohexane, chloroform, etc., or with mixtures thereof. The esterification reaction is usually performed at a temperature of 0° C to 75° C, usually at room temperature and atmospheric pressure, or at higher pressures, with the prostaglandin ester recovered by evaporation of the solvent and like techniques. The esterification reaction is described in *Organic Chemistry,* by Fieser and Fieser, pages 180 to 181, 1944.

The esterification of the prostaglandins (when $R_1,R_2=H$) can also be carried out by forming a salt of the organic acid followed by reacting the salt with a hydrocarbyl halide. For example, the silver salts of the prostaglandin is made by art known processes, such as dissolving the prostaglandin in cold, diluted aqueous ammonia, next, evaporating the excess ammonia in vacuo, and then adding stoichiometric amounts or an excess of silver nitrate, followed by reacting the salt with a suitable halide such as methyl iodide, butyl iodide, iso-propyl iodide, tert-butyl iodide, benzyl iodide, and the like; *Textbook of Organic Chemistry,* Richter, G. H., 1952, John Wiley & Sons.

The hydroxyl group of the prostaglandins at position C-15 can be esterified by reacting an acylating agent with the hydroxyl group in an organic medium. Examples of acylating agents suitable for esterifying the hydroxyl group include anhydrides, mixed anhydrides, chlorides of alkanoic acids and the like. Exemplary anhydrides include acetic anhydride, butyric anhydride, propionic anhydride, iso-propionic anhydride and the like. Exemplary acid chlorides include acetyl chloride, propionyl chloride, iso-propionyl chloride, butyryl chloride, decanoyl chloride, succinyl chloride, acryloyl chloride and the like. The acylation is carried out by contacting and reacting the prostaglandin bearing the hydroxyl group with, for example, an acid anhydride in the presence of a solvent, for example, triethylamine, trimethylamine, pyridine or the like at a temperature of 5° C to 75° C, usually at 25° C for 12 hours to 60 hours and at a pressure of 1 atmosphere to 5 atmosphere or higher. Generally, the reactants are present in equivalent amounts or in excess thereof, for example, 1 to 10 moles of anhydride to 1 mole of hydroxyl reactant. The acylated product is recovered by decomposing the unreacted acylating agent with water and extracting with an organic solvent, such as ether, and isolating the acylated compound by evaporating the solvent.

The prostaglandins as embraced by the above Formula 1 can be converted to its non-toxic, pharmaceutically acceptable salt ($R_1=H$) by neutralizing the prostaglandin with an equivalent or an excess amount of the corresponding non-toxic salt forming organic or inorganic base. The salts are prepared by procedures known to the art, for example, equivalent or stoichiometric quantities of the prostaglandin and the organic base are dissolved in an inert organic solvent at room temperature or in a warmed solvent with a gentle mixing of the reacting prostaglandin and the base until all the reactants are in solution. The product or salt is obtained by chilling the resulting mixture to precipitate the powder or crystals, or the product can be isolated by the addition of a miscible diluent of low polarity, or by the use of standard evaporation techniques. The formation of inorganic prostaglandin salts is also carried out by procedures known to the art; for example, the prostaglandin is dissolved in an aqueous solution containing stoichiometric amounts or an excess amount of a non-toxic salt forming inorganic hydroxide, carbonate or the like. This reaction can be carried out in the presence of an inert organic solvent, and the product is obtained by procedures such as the evaporation of the aqueous medium, or the organic medium, by the addition of miscible solvents of low polarity, or by chilling the mixture to precipitate the product.

The following examples are set forth as representative methods of the spirit of the invention. These examples are not to be construed as limiting the scope of the invention as other functionally equivalent means will be readily apparent to those skilled in the subject art in the light of the present specification and accompanying claims.

EXAMPLE 1

Preparation of methyl 15(R)-acetoxy-9-oxo-5-cis,10,13-transprostatrienoate, the methyl acetate diester of 15-epi-PGA$_2$, as depicted in Formula 2. First, 450 grams of gorgonian *Plexaura homomalla* is freshly dried at room temperature and the cortex stripped from the inner skeleton. Then, the removed cortex is ground to a fine mesh, and the ground cortex is extracted with commercially available, standard grade hexane. The cortex is extracted by placing the ground cortex in a conical filter funnel equipped with filter paper and extracted with hexane by passing the hexane over the ground cortex until the resulting solution showed no observable color. The excess solvent from the extraction is removed on a conventional rotary evaporator, and the last traces of solvent are removed using a standard high vacuum pump until a constant weight is recorded. About 43 grams of hexane extractables are extracted from the employed quantity of gorgonian.

Next, the hexane extract is subjected to conventional fractionation techniques. The fractionation technique employed consists of a first column chromatography using a 2.5 inch diameter column packed with 490 grams of silicic acid, commercially available as SilicAR° CC-7, using benzene as the solvent for the packing procedure. Next, 83 grams of the crude extract obtained according to the procedure described immediately above, is placed on the column in a benzene solution and it is washed onto the column with more benzene. The crude extract is then eluted from the column using measured volumes of solvents of increasing polarity as follows: first, 4000 ml of benzene; second 1000 ml of 20% ethylacetate in benzene; third, 1000 ml of 40% ethylacetate in benzene; fourth, 1000 ml of 60% ethyl acetate in benzene; and, fifth, 1000 ml of ethylacetate. The percent recovered is 90.6.

Further purification and isolation of the compound is carried out as follows: first, 70 grams of silicic acid (CC-4) is packed into a 1.25 inch diameter column as a benzene slurry. After preparing the column, it is washed with about 500 ml of benzene. Next, 1.5 grams of the sample obtained from the 20% ethyl acetate in benzene fraction of the 2.5 inch column is washed into the smaller 1.25 inch column, with benzene. The fraction is eluted from the latter column by using 8% ethyl acetate in benzene, and at a flow rate of 2 ml per minute, and 13 fractions of 50 ml each were taken. Fractions 6 to 12 contain the prostaglandin diester. Thin layer chromatography is used to identify the diester. The analytical results are as follows: high resolution mass spectrum (m-60=330.2187; i.e., $C_{21}H_{30}O_3$): the mass spectrum showed peaks at m/e of 390, 359, 330 and 190 (base peak); ORD spectrum (CH$_3$OH) peak at 247 mμ and through at 218 mμ; uv max (MeOH) 215 mμ, ε=9,300. The IR spectra shows peaks at IR (film) 1735, 1710, 1585, 1455, 1435, 1370, 1310, 1240, 1165, 1015, 965, 885, 810, and 720 cm$^{-1}$ and IR (CHCl$_3$) 1730, 1710, 1585, 1455, 1435, 1370, 1310, 1240, 1205, 1170, 1145, 1015, 965, and 880 cm$^{-1}$. The NMR spectrum (CCl$_4$) shows peaks δ7.44 (1,dd,J=z,6Hz), 6.12 (1,dd,J=2,6Hz), 5.48 (4 proton vinyl envelopes), 5.14 (1,m), 3.61 (3,6), 1.98 (3,S), and 0.89 (3, perturbed triplet).

EXAMPLE 2

Preparation of methyl 15(R)-acetoxy-9-oxo-5-cis,13-trans-prostadienoate. First, a 0.885 gram, (2.27 mmole) sample of methyl 15(R)-acetoxy-9-oxo-5-cis,10,13-trans-prostatrienoate, as prepared according to Example 1, was dissolved, with constant stirring, in 16 ml of commercially available ethyl acetate, having a density of 0.885 (g/ml at 25° C). Then, 0.10 grams of rhodium catalyst, (5% supported on carbon), was added to the mixture and it was cooled to 0° C. A vacuum was applied to the mixture to remove oxygen, and the mixture was magnetically stirred during the evacuation to aid in removing oxygen from the mixture. The apparatus containing the mixture was then filled with hydrogen gas, evacuated, and the evacuation procedure repeated three times followed by the addition of hydrogen to assure the absence of oxygen from the apparatus. After the last evacuation, the reaction mixture was magnetically stirred at 0° C under one atmosphere of hydrogen pressure for approximately 3½ hours. Samples of the reaction mixture were periodically taken and analyzed by silver nitrate thin layer chromatography (TLC) and by mass spectroscopy. After about 3½ hours, the TLC analysis did not show any starting material in the reaction mixture.

The reaction mixture was filtered through Celite®, diatomaceous silica, with ethyl acetate washings under vacuum. On concentration in vacuo of the ethyl acetate solution, 0.874 grams of crude product was recovered. The product was chromatographed on 50 grams of 10% silver nitrate impregnated SilicAR® CC-4, 100–200 mesh, in a ⅜ inch diameter column using 10% ethyl acetate in hexane to elute the product. The eluent was analyzed by thin layer chromatography and after approximately 1000 ml were collected, the product (0.4029 gm) was eluted in the next 1000 ml of eluent. The product, methyl 15 (R)-acetoxy-9-oxo-5-cis,13-trans-prostadienoate, showed mass spectrum peaks at 392 (M+) and 332 (M-60). The nuclear magnetic resonance (NMR) spectrum showed a loss of characteristic absorptions of the starting material at δ7.4, 6.1 and 3.2 attributed to the absence of the 10,11 carbon carbon double bond, due to the absorption of one mole equivalent of hydrogen, while retaining the other characteristic signals of the starting compound methyl 15(R)-acetoxy-9-oxo-5-cis,10,13-trans-prostatrienoate.

EXAMPLE 3

Preparation of methyl 15 (R)-acetoxy-9-oxo-13-trans-prostenoate. A 0.252 gram, (0.65 mmole) sample of methyl 15 (R)-acetoxy-9-oxo-5-cis,10,13-trans-prostatrienoate, prepared according to Example 1,was dissolved in 8 ml of ethyl acetate containing 65 mg of 5% rhodium on carbon and hydrogenated under one atmosphere at 25° C for 1 hour. The reaction mixture was filtered through Celite® under vacuum with ethyl acetate washings. After concentration of the solvent, 0.226 grams of oily product was recovered. Analysis of the product by silver nitrate thin layer chromatography showed no remaining starting material. The product was chromatographed on a column containing 10 grams of 10% silver nitrate impregnated SilicAR® CC-4, using 8% ethyl acetate in hexane as the elutant, and it was eluted in fractions 8 through 14 (15 ml each). The mass spectrum showed peaks at 394 (M+) and 334 (M-60), and the NMR spectrum showed loss of signals characteristic of the C-5 and C-10 double bonds of the starting material, while retaining the signal for the trans C-13 double bond.

EXAMPLE 4

Preparation of diastereomeric methyl 15-formoxy-9-oxo-5-cis, 13-trans-prostadienoate. A 300 mg sample of methyl 15(R)-acetoxy-9-oxo-5-cis,13-trans-prostadienoate as prepared according to Example 2 is dissolved in a reaction medium obtained by reacting 8 ml of formic acid and 80 mg of potassium carbonate to form in situ potassium formate, and the mixture constantly stirred to ensure a contacting of the reactants. The reaction is allowed to proceed for about 70 hours at room temperature and then the solvent is evaporated on a rotary evaporator at about 30° C with in-house vacuum assist. Next, about 20 ml of toluene is added to the residue and the mixture shaken and again evaporated to remove any remaining formic acid. The residue is taken up in 50 ml of benzene and filtered with benzene washing to eliminate inorganic salts. The solvent is again evaporated to give a mixture of diastereomeric formates as determined by NMR spectroscopy. The product mixtue weighed about 0.290 grams.

EXAMPLE 5

Preparation of diastereomeric methyl 15-formoxy-9-oxo-13-trans-prostenoate. A 200 mg sample of diastereomeric methyl 15(R)-acetoxy-9-oxo-b 13-trans-prostenoate as prepared according to Example 3 is dissolved in a reaction medium obtained by reacting 8 ml of formic acid and 80 mg of potassium carbonate to form in situ potassium formate and the mixture constantly stirred to ensure a contacting of the reactants. The reaction is allowed to proceed for about 70 hours at ambient conditions and then the solvent evaporated on a rotary evaporator at about 30° C with in-house vacuum assist. Next, about 20 ml of toluene is added to the residue and the mixture shaken and again evaporated to remove the remaining formic acid. The residue is then filtered through a small column with an inside diameter of 1.0 inches containing 30 grams of silicic acid, commercially available as SilicAR® CC-7, using 20% ethyl acetate in benzene as the eluting solvent. The solvent is again evaporated to give a crude weight of 0.180 grams of a mixture of diastereomeric formates.

EXAMPLE 6

Preparation of diastereomeric methyl 15-hydroxy-9-oxo-5-cis,13-trans-prostadienoate. A 56 mg sample of the product prepared according to the procedure of Example 4 is dissolved in 10 ml of a freshly prepared mixture consisting of 95 % dry methanol and 5% 1N hydrochloric acid with slight stirring to ensure a complete mixing of the ingredients. Next, the solution is magnetically stirred at room temperature and pressure for about 24 hours. The product is then recovered from the reaction solution by first removing most of the methanol by stripping in vacuo, followed by adding 50 ml of ethyl acetate to the residue and extracting the ethyl acetate residue mixture three times with 10 ml portions of 50% brine. The organic, ethyl acetate phase, with washings, were combined, dried over anhydrous MgSO$_4$ and evaporated to yield 0.048 grams of a mixture of diastereomeric methyl 15-hydroxy-9-oxo-5-cis,13-trans-prostadienoate. These diastereomers are separated by column chromatography.

EXAMPLE 7

Preparation of 15(S)-hydroxy-9-oxo-13-trans-prostenoic acid. First, 0.25 grams of methyl 15-formoxy-9-oxo-13-trans-prostenoate, as prepared according to Example 5, was dissolved in 20 ml of methanol containing 0.36 grams of potassium hydroxide and the reaction mixture magnetically stirred for about 3 hours. Next, the reaction mixture was acidified with 1N HCl and 20 ml of saturated brine added to the acidified reaction mixture. Next, the aqueous phase was extracted 5 times with 50 ml aliquots of chloroform, and the organic phases dried over anhydrous magnesium sulfate. The organic phases were then combined and concentrated in vacuo to yield 0.20 grams of crude product. The diastereomers were separated on a 20 gram column of, commercially available, SilicAR® CC-4 using 20% ethyl acetate in benzene to elute the isomers. The first isomer eluted was 15(R)-hydroxy-9-oxo-13-trans-prostenoic acid, which was followed by 15(S)-hydroxy-9-oxo-13-trans-prostenoic acid.

EXAMPLE 8

Preparation of 15(S)-hydroxy-9-oxo-5-cis,13-trans-prostadienoic acid. A 0.25 gram sample of methyl 15(S)-hydroxy-9-oxo-5-cis,13-trans-prostadienoate, prepared according to Example 6, was dissolved in 20 ml of methanol containing 0.36 grams of potassium hydroxide and the mixture stirred for 2½ to 3½ hours. Next, the reaction mixture was acidified with 1N HCl, and 20 ml of saturated brine added to the acidified mixture. Then, the aqueous phase was extracted with chloroform and dried over anhydrous sulfate, filtered, and the organic phase stripped in vacuo to yield 0.22 grams of product.

EXAMPLE 9

Preparation of propyl 15(S)-hydroxy-9-oxo-5-cis,14-trans-prostadienoate. A solution of 1 mole of 15(S)-hydroxy-9-oxo-5-cis,13-trans-prostadienoic acid in a mixture of 10 ml of dry methanol and 90 ml of dry diethyl ether is mixed at room temperature with an excess of diazopropane in diethyl ether and allowed to stand for about 60 minutes. The mixture is evaporated to dryness under reduced in-house pressure to obtain the product comprising propyl 15(S)-hydroxy-9-oxo-5-cis,13-trans-prostadienoate.

EXAMPLE 10

Following the procedure of Example 9 but substituting for diazopropane other diazoalkanes, for example, diazoethane, diazobutane, diazohexane, and the like, to produce esters such as ethyl 15(S)-hydroxy-9-oxo-5-cis,13-trans-prostadienoate, butyl 15-hydroxy-9-oxo-5-cis,13-trans-prostadienoate, hexyl 15-hydroxy-9-oxo-5-cis,13-trans-prostadienoate, and the like.

EXAMPLE 11

Preparation of 15(S)-propionyloxy-9-oxo-5-cis,13-trans-prostatrienoic acid. To a three neck flask is added 0.1 mole of 15(S)-hydroxy-9-oxo-5-cis,13-trans-prostadienoic acid, 10 ml of propionic anhydride and 10 ml of pyridine and the reaction medium allowed to stand at room temperature for 4 hours. Next, the mixture is concentrated to dryness under reduced in-house vacuum to give 15 propionyloxy-9-oxo-5-cis,13-trans-prostadienoic acid, which is purified by chromatography over synthetic magnesium silicate using as the eluent n-hexane, b. 60°-68° C containing increased amounts of acetone.

EXAMPLE 12

Following the procedure of Example 11 but substituting for propionic anhydride, butyric anhydride, acetic anhydride, succinyl chloride and the like, the corresponding acylated compound is produced by the interaction of the hydroxyl group with the respective acylating agent.

The novel compounds of the invention are useful for preparing other valuable prostaglandins and as pharmaceutical agents. The utility of the novel compounds of the invention as intermediates is set forth in Table I.

In Table I, methyl 15(R)-acetoxy-9-oxo-5-cis,10,13-trans-prostatrienoate, (compound A,$R_1$=Methyl and $R_2$=Acetoxy), is subjected to hydrogenation to produce methyl 15(R)-acetoxy-9-oxo-5-cis,13-trans-prostadienoate (B). Compound B is subjected to epimerization to produce methyl 15(S)-formoxy-9-oxo-5-cis,13-trans-prostadienoate (C) which is subjected to hydrolysis to yield methyl 15(S)-hydroxy-9-oxo-5-cis,13-trans-prostadienoate (E), which compound is therapeutically useful as an antihypertension agent. Additionally, compound A can be subjected to hydrolysis to give methyl 15(R)-hydroxy-9-oxo-5-cis,10,13-trans-prostatrienoate (D), which is hydrogenated, epimerized, and hydrolyzed to give methyl 15(S)-hydroxy-9-oxo-5-cis,13-trans-prostadienoate (E). Compound E can be saponified to yield 15(S)-hydroxy-9-oxo-5-cis,13-trans-prostadienoic acid (compound F,$R_1$=H) which is useful as an antihypertension agent. Compound E or F can be hydrogenated to give compounds methyl 15(S)-hydroxy-9-oxo-13-trans-prostenoate (G) and 15(S)-hydroxy-9-oxo-13-trans-prostenoic acid (compound H,$R_1$=H). Compound G can be hydrolyzed to H, while H can be esterified to G, both of which are useful as antihypertension agents.

The novel prostaglandins as embraced by Formula 1 are therapeutically useful as antihypertension agents,

TABLE I

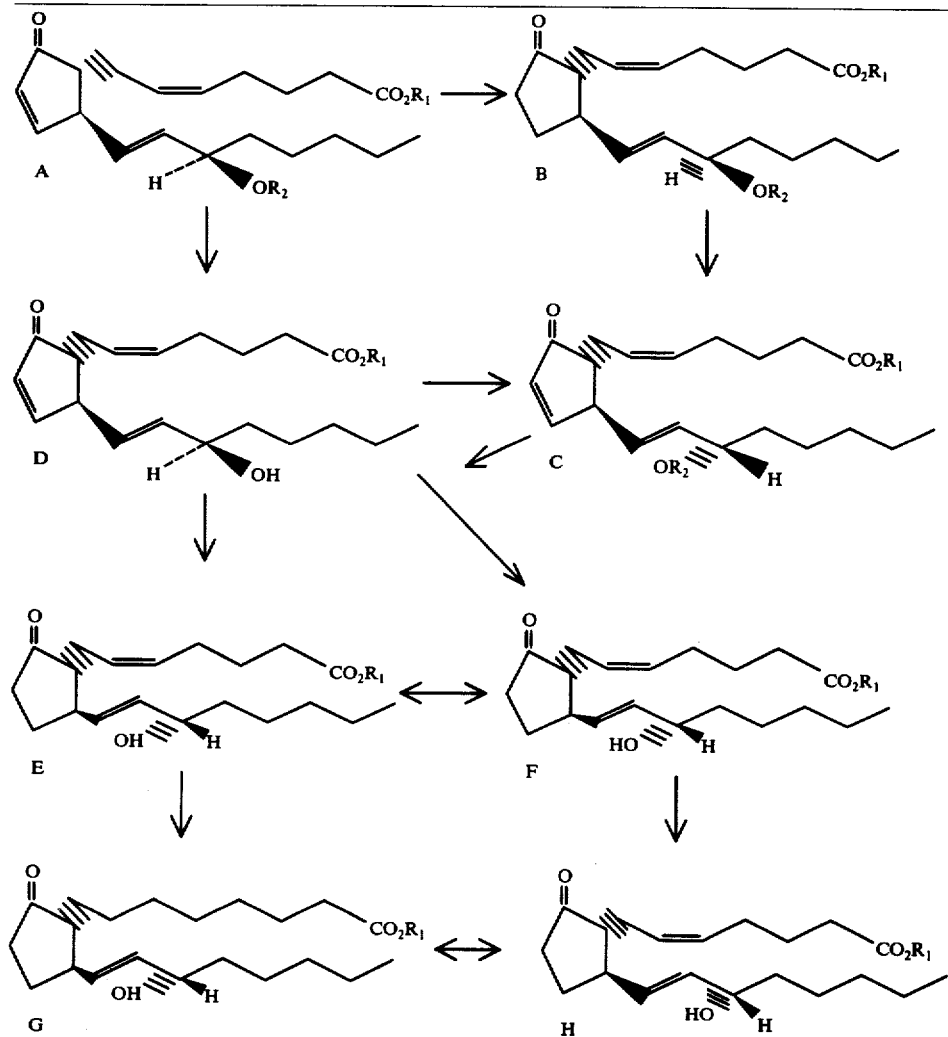

that is, they are useful for the management of high blood pressure without effecting smooth muscle activity in mammals, including avians, primates, household animals, valuable farm animals, laboratory animals, and the like. The novel prostaglandins can be administered in a variety of pharmaceutical forms, that is, as a pharmaceutical carrier. The prostaglandins can be formulated into tablets, capsules, elixers, drug delivery devices, syrups, drops, powders, injectable preparations, ointments, and the like. The pharmaceutical carriers can be non-toxic inorganic or non-toxic organic carriers, solid or liquid, and the pharmaceutical compositions can be administered enterally, parenterally, and the like. Examples of pharmaceutical carriers include water, saline, gelatin, sugar, such as lactose, glucose, sucrose, starches, such as corn starch and arrowroot, stearic acid or salts thereof, such as magnesium or calcium stearate, talc, vegetable fats or oils, gums, alginic acid, benzyl alcohols, glycols and other known recipients. The pharmaceutical compositions may be sterilized and also contain adjuvants such as preserving, stabilizing, wetting, emulsifying agents and the like.

An example of a typical method for preparing a pharmaceutical form for the preparation of a tablet containing the active new prostaglandin, is to first suitably comminute the active ingredient with a diluent such as starch, sucrose, kaolin or the like to form a powder mixture. Next, the just prepared mixture can be granulated by wetting with a non-toxic binder such as a solution of gelatin, acacia mucilage, corn syrup, mixtures thereof, and the like, and after mixing the composition is screened to any predetermined particle sieve size. As an alternative, if preferred to granulation, the just prepared mixture can be slugged through conventional tablet machines and the slugs comminuted before the fabrication of the tablets. The freshly prepared tablets can be coated or they can be left uncoated. Representative of suitable coatings are the non-toxic coatings including shellac, methyl-cellulose, carnauba wax, styrene-maleic copolymers, and the like. For oral administration, compressed tablets containing 0.01 micrograms, 1 milligram, 5 milligrams, 50 milligrams, etc., of prostaglandin are manufactured in the light of the above disclosure and by fabrication techniques well known to the art and set forth in *Remington's Pharmaceutical Science*, Chapter 39, Mac Publishing Co., 1965. A typical formulation for a tablet containing a prostaglandin, for example, 15-hydroxy-9-oxo-5-cis,13,-trans-prostadienoic acid, is described in Example 13.

EXAMPLE 13

|  | Per Tablet, mg |
| --- | --- |
| Prostaglandin | 2.0 |
| Corn Starch | 15.0 |
| Corn Starch Paste | 4.5 |
| Lactose | 82.0 |
| Calcium Stearate | 2.0 |
| Dicalcium Phosphate | 50.0 |

To formulate the tablet, uniformly blend the prostaglandin, corn starch, lactose, and dicalcium phosphate in a V-blender until all the ingredients are uniformly mixed together. Next, the corn starch is prepared as a 10% aqueous paste and it is blended with the uniform mixture until a second uniform mixture is obtained. Then, the wet granulation is passed through a standard eight mesh screen, dried and rescreened with a twelve mesh screen. The dry granules are next blended with calcium stearate and compressed into tablets. Other tablets containing 0.05 mg, 2 g, 4 g, 10 g, b 15 g, etc., are prepared in a like fashion.

The pharmaceutical manufacture of capsules for oral use consists essentially of mixing the active compound with a non-toxic carrier and enclosing the mixture in a gelatin sheath. The capsules can be in the art known soft form of a capsule made by enclosing the compound in intimate dispersion within an edible oil or the capsule can be a hard capsule consisting essentially of the novel compound mixed with a non-toxic solid, such as talc, calcium stearate, calcium carbonate or the like. A typical capsule formulation is described in Example 14.

EXAMPLE 14

Capsules containing 0.1 mg, 10.0 mg, 15 mg, 20 mg, 1 g, 2 g, and the like, of prostaglandin, for example, methyl 15-hydroxy-9-oxo-5-cis,13-trans-prostadienoate, are prepared by blending the following:

| | |
| --- | --- |
| Prostaglandin | 5.0 |
| Lactose U.S.P. | 300.0 |
| Starch | 130.0 |
| Magnesium Stearate | 4.5 |

The blended ingredients are discharged into a commercially available capsule, and with the higher concentrations of prostaglandin as the active ingredient in the capsule, a suitable reduction is made in the amount of lactose, or another appropriate non-toxic, inert ingredient, for example, talc, can be added thereto.

The daily dose administered for the novel compounds will, of course, vary with the particular novel prostaglandin employed because of the varying potency of the compounds, the chosen route of administration and the size of the recipient. The dosage administered is not subject to definite bounds, but it will usually be an effective amount or the equivalent on a molar basis of the pharmacologically active free acid form of the prostaglandin to produce the desired physiological or pharmacological effects. Representative of a typical method for administering to a mammal the prostaglandins of the invention is by the oral route. By this route, 10 $\mu$g to 1000 $\mu$g per kg of recipient per day is administered to evoke the desired antihypertension effects. Another method for administering the prostaglandins, for example, diastereoisomeric methyl 15-hydroxy-9-oxo-5-cis,13-trans-prostadienoate, is by the injectable-type administration route. By this route, a sterile solution containing the compound is administered intravenously or subcutaneously at the rate of 10 micrograms to 450 micrograms per kilogram of body weight per minute by means of an infusion pump to raise the blood pressure at the rate of 1 to 20 milliter per hour. The compound is administered by the injectable route in a form suited for injection, such as mixed with sterile physiological saline, or in aqueous solutions for subcutaneous administration having incorporated therein an agent that delays absorption such as aluminum monostearate and the like.

Suitable topical preparations can easily be prepared by, for example, mixing 500 mg to 1500 mg and the like, of the prostaglandins with 15 g of cetyl alcohol, 1 g of sodium lauryl sulfate, 40 g of liquid silicone D. C. 200, sold by Dow Corning Co., Midland, Michigan, 43 g of sterile water, 0.25 g of methylparaben and 0.15 g of propylparaben and warming the mixture with constant stirring to about 75° C and then permitting the preparation to congeal. The preparation can be readily applied to the skin by inunction or it can be applied topically by dispensing the preparation from a conventional surgical gauze dispenser, adhesive bandage, and the like.

For administering to valuable domestic household, sport or farm animals, such as sheep, goats, cattle, etc., or for administering to laboratory animals such as mice, rats, guinea pigs, monkeys, etc., for scientific studies, the new compound is prepared in the form of a food premix, such as mixing with dried fish meal, oatmeal, straw, hay, ground corn, mash, and the like, and then the prepared premix is added to the regular feed, thereby administering the compound to the domestic or laboratory animal in the form of feed. The prostaglandin can also be administered to laboratory animals in laboratory studies for determining the therapeutic utility and application of the prostaglandin to mammals, including humans, avians, farm animals and sport animals, by other well known methods. For example, in laboratory studies with standard white laboratory rats the compounds, for example, diastereoisomeric 15-propoxy-9-oxo-5-cis,13-trans-prostadienoic acid, can be administered orally by perfusion in saline at the rate of 5 micrograms to 50 micrograms per kg of rat body weight per minute across the mucosal surface of the stomach to study the lowering of blood pressure, its regulatory effects on salt, water, lipids, and gastric secretion.

The above examples and disclosures are set forth merely for illustrating the mode and the manner of the invention and various modifications and embodiments can be made by those skilled in the art in the light of the invention without departing from the spirit of the invention.

I claim:

1. A topical pharmaceutical preparation comprising 500 mg to 1500 mg of diasteroisomeric 15-propionyloxy-9-oxo-5-cis, 13-trans-prostadienoic acid mixed with 15 g of cetyl alcohol, 1 g of sodium lauryl sulfate, 40 g of liquid dimethylpolysiloxane, 43 g of sterile water, 0.25 g of methylparaben and 0.15 g of propylparaben.

* * * * *